United States Patent
Camarda et al.

(10) Patent No.: US 6,578,003 B1
(45) Date of Patent: *Jun. 10, 2003

(54) METHOD AND APPARATUS FOR IMPROVING PATIENT COMPLIANCE WITH PRESCRIPTIONS

(75) Inventors: Leonard T. Camarda, Bedminster, NJ (US); Curtis S. Wilbur, Hopewell, NJ (US); Stephen B. Schectman, Summit, NJ (US); Gregory K. Hanson, Edina, MN (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/562,408

(22) Filed: May 1, 2000

Related U.S. Application Data

(63) Continuation of application No. 09/126,369, filed on Jul. 30, 1998.
(60) Provisional application No. 60/082,172, filed on Apr. 16, 1998, and provisional application No. 60/054,384, filed on Jul. 31, 1997.

(51) Int. Cl.⁷ .............................................. G06F 17/60
(52) U.S. Cl. ............................................... 705/3; 705/2
(58) Field of Search .......................................... 705/3, 2

(56) References Cited

U.S. PATENT DOCUMENTS 5,547,878 A * 8/1996 Kell ........................... 436/111

(List continued on next page.)

FOREIGN PATENT DOCUMENTS

EP 0 301 672 * 9/1989

(List continued on next page.)

OTHER PUBLICATIONS

"Recipe for Research and Development success—'Get Lucky';" Scrip 2117; p. 8; Apr. 5, 1996.*

(List continued on next page.)

*Primary Examiner*—Jeffrey A. Smith
*Assistant Examiner*—Forest Thompson, Jr.
(74) *Attorney, Agent, or Firm*—Darby & Darby; Immac J. Thampoe

(57) ABSTRACT

A method and apparatus for improving patient compliance with prescriptions utilizes computer terminals to convert prescription information into electronic form as records for each patient. Each such patient record includes information about the patient from the prescription and the prescription itself. In addition, demographic information about the patient is obtained from other commercial databases and added to the patient record. Then a regression analysis is run on the patient records using the various data elements versus the compliance of the patient with the prescription to determine the relative importance of each variable in the prediction. The analysis is used to segregate the patients into demographic clusters and to associate champion intervention messages with each cluster. When a patient's prescription is entered in the system thereafter, the model is used to associate the patient with a cluster and to direct the champion message to that patient. Further, a regression analysis may be run on the patient data to create a model of likelihood of prescription compliance in general by the patient. The result is a probability equation that allows a score to be assigned to each record. Based on this score, the patients most likely to fail to comply with their prescription are sent the champion interventions. As new challenge interventions messages are created additional information is gathered and the regression analysis is re-run. If the challenge message is more successful, it is substituted as the new. champion message. The results of these interventions are recorded and appended to the related patient record.

9 Claims, 7 Drawing Sheets

U.S. PATENT DOCUMENTS

| | | | | |
|---|---|---|---|---|
| 5,594,637 A | * | 1/1997 | Eisenberg et al. | 705/2 |
| 5,612,869 A | * | 3/1997 | Letzt et al. | 705/3 |
| 5,623,242 A | * | 4/1997 | Dawson et al. | 340/7.3 |
| 5,664,109 A | * | 9/1997 | Johnson et al. | 705/3 |
| 5,666,492 A | * | 9/1997 | Rhodes et al. | 705/3 |
| 5,722,418 A | * | 3/1998 | Bro | 128/905 |
| 5,748,907 A | * | 5/1998 | Crane | 705/2 |
| 5,772,585 A | * | 6/1998 | Lavin et al. | 705/3 X |
| 5,832,488 A | * | 11/1998 | Eberhardt | 707/10 |
| 5,908,788 A | * | 6/1999 | Kell | 436/111 |
| 5,933,136 A | * | 8/1999 | Brown | 705/3 |
| 5,974,396 A | * | 10/1999 | Anderson et al. | 705/10 |
| 5,976,082 A | * | 11/1999 | Wong et al. | 600/300 |

FOREIGN PATENT DOCUMENTS

| | | | |
|---|---|---|---|
| EP | 0 403 294 | * | 12/1990 |
| EP | 0 526 166 A2 | * | 2/1993 |
| EP | 0 592 851 A2 | * | 4/1994 |
| EP | 0 789 307 A1 | * | 8/1997 |

OTHER PUBLICATIONS

"Microsoft Press Computer Dictionary;" Microsoft press; 1997.*

Bean, Andrew G. ; Talaga, James, "Appointment Breaking: Causes and solutions" J. Health Care Marketing 12:14 (Dec. 1992).

McElnay, JC et al "Self–reported medication non–compliance in the ederly," Eur. J. Clinical Pharmacology 53:171 (1997).

Burns, Lawton R.; Chillingerian, Jon A.; "The effects of physician practice organization on efficient utilization of hospital resources;" Health Services Research; v29n5, p. 583–603; Dec. 1994.*

* cited by examiner

SUB-POPULATION - FIRST FILL

SCORECARD PREDICTIVE POWER

| CHARACTERISTICS | MAIN SAMPLE PRED. POWER | HOLDOUT SAMPLE PRED. POWER |
|---|---|---|
| NUMBER OF REFILLS ALLOWED CURRENT Rx | 0.114 | 0.116 |
| NUMBER OF DAYS SUPPLY CURRENT Rx | 0.013 | 0.019 |
| AGE OF PATIENT | 0.047 | 0.032 |
| SEASONAL LETTER SENT IN PAST (y/n) | 0.013 | 0.003 |
| MONTH OF CURRENT FILL | 0.021 | 0.042 |
| STORE STATE | 0.020 | 0.017 |
| QUANTITY DISPENSED | 0.011 | 0.017 |
| DAY OF THE WEEK OF CURRENT FILL | 0.007 | 0.001 |
| INFORMATION VALUE | 0.296 | 0.283 |
| K-S @ SCORE -40 | 20.3 | |

SUMMARY STATISTICS

| | COMPLIANT | NOT COMPLIANT | TOTAL |
|---|---|---|---|
| TOTAL SAMPLE: | 3239 | 9151 | 13448 |
| MEAN SCORE: | -22.17 | -41.61 | -35.60 |
| STD. DEV.: | 34.01 | 37.76 | 37.71 |
| MIN. SCORE: | -135 | -166 | -166 |
| QUARTILE1 SCORE | -43 | -68 | -60 |
| MEDIAN SCORE | -19 | -37 | -31 |
| QUARTILE3 SCORE | 0 | -13 | -9 |
| MAX. SCORE: | 114 | 71 | 114 |

FIG. 5

AND THE BEST MESSAGES ARE...      RESPONSE RATE

- IMPORTANCE OF PROPHYLACTIC USE — 66.1 %
- BE PREPARED/DON'T GET CAUGHT WITHOUT — 85.0 %
- QUALITY OF LIFE — 63.4 %
- ACTIVE LIFESTYLE — 61.2 %
- IMPACT ON PRODUCTIVITY/LEARNING — 80.3 %
- CONTROL OVER LIFE — 71.1 %
- SERIOUSNESS OF HEALTH CONDITION — 79.1 %
- SAFETY - MINIMUM SIDE EFFECTS — 66.7 %
- MAY COST MORE, BUT WORTH IT — 82.2 %

CONTROL GROUP — 60.4 %

FIG. 6

| DECILE | NUMBER OF FILLS | NUMBER OF 'COMPLIANT' FILLS | COMPLIANCE RATE |
|---|---|---|---|
| 10 | 2191 | 218 | 10% |
| 20 | 2242 | 345 | 15% |
| 30 | 2149 | 429 | 20% |
| 40 | 2189 | 509 | 23% |
| 50 | 2273 | 586 | 26% |
| 60 | 2203 | 626 | 28% |
| 70 | 2228 | 718 | 32% |
| 80 | 2221 | 888 | 40% |
| 90 | 2253 | 1217 | 54% |
| 100 | 2220 | 1579 | 71% |
| TOTAL | 22169 | 7115 | 32% |

FIG. 7

| DECILE | FIRST FILL COMPLIANCE RATES | SECOND OR GREATER FILL COMPLIANCE RATES |
|---|---|---|
| 10 | 9% | 11% |
| 20 | 14% | 18% |
| 30 | 19% | 26% |
| 40 | 22% | 31% |
| 50 | 23% | 43% |
| 60 | 26% | 51% |
| 70 | 25% | 55% |
| 80 | 30% | 60% |
| 90 | 33% | 68% |
| 100 | 39% | 79% |
| AVERAGE | 24% | 44% |

FIG. 8

METHOD AND APPARATUS FOR IMPROVING PATIENT COMPLIANCE WITH PRESCRIPTIONS

This application is a continuation of U.S. Ser. No. 09/126,369 filed Jul. 30, 1998, which claims the benefit of U.S. provisional application No. 60/054,384 filed Jul. 31, 1997 and No. 60/082,172 filed Apr. 16, 1998.

Throughout this disclosure, various publications, patents and patent applications are referenced. The disclosures of these publications, patents and patent applications are herein incorporated by reference.

FIELD OF THE INVENTION

The present invention relates to disease management in general and, more particularly, to methods and apparatus for improving patients' compliance with prescriptions for medication that they are given to improve a disease condition.

BACKGROUND OF THE INVENTION

It is quite common in the treatment of a disease condition for a health care provider to prescribe certain medications for the treatment of the condition. The medications must be taken in specific doses at particular times of day over a course of time in order to insure that they have the maximum effect on the health condition of the patient. In addition, the doctor or other health care provider may prescribe other courses of conduct to effect the disease or condition, e.g., diets, exercise or lifestyle changes. Thus, "compliance" as used herein, is interchangeable with adherence, and means the extent to which a person's behavior in terms of medications, following diets, or executing lifestyle changes coincides with medical and health advice.

The patient is usually responsible for compliance with the prescription. If the patient fails to comply with the prescription, it is likely that the condition will not improve, or at least not improve as quickly as possible. This, of course, results in an adverse consequence for the patient and his family. Also, the continued poor health condition of the patient has a negative effect on the patient's employer, which in turn has a negative effect on the economy in general because the patient may not be able to work at all, or to work as efficiently.

Failure to take the medication as prescribed is typically due to the fact that the patient has not filled the prescription at a pharmacy. This results in a loss of income to the pharmacy. If the patient takes only part of the prescribed medication, the results may not be satisfactory, and the patient and health care provider may assume that the medication is ineffective. If this view is shared with others, it can have a negative impact on the sale of the medication, which could harm the manufacturer of the medication unfairly.

Patients who do not take their prescribed medication also place additional burdens on the health care system in which the patient is enrolled because they stay ill longer, which increases the medical services that must be provided to the patient and the attendant cost. The health care system may be a private medical plan, perhaps supported by an employer, or the government. Where the medical plan is a managed care organization ("MCOs"), such as an HMO, a PPOs, etc., this burden may be critical, because such organizations are required to manage care in a cost effective and high quality way to be competitive. Also, when a patient remains ill longer than necessary, they may get worse and require emergency room treatment, which is perhaps the most expensive way to handle a disease condition. Further the ineffectively treated condition may lead to other and more serious complications, which again reduces the quality of life of the patient, reduces the patient's ability to contribute work effort to his employer, and generally increases costs for treatment.

It is estimated by the National Association of Chain Drug Stores ("NACDS") that 50% of all prescriptions dispensed in the U.S. are not taken correctly, and that non-compliance with prescription medications costs Americans between $50 billion and $100 billion each year in increased hospitalization and long-term health complications. The NACDS also notes that pharmacist intervention improves compliance and outcomes, and consequently lowers health care costs.

Disease Management is a new area of medicine which focuses on organizing the treatment of patients according to the disease or condition the patient may have so that services are delivered to the patient in a way that is most effective, and utilizes the most appropriate and cost effective service delivered by the most appropriate health care provider needed at the time. One aspect of disease management is to assure, as best as possible, that the patient complies with the prescription. However, in most cases, because the patient has the primary responsibility for this, it is difficult to track this compliance and intervene, e.g. when a course of medication is not being followed. Thus, it would be helpful if indications of lack of compliance were available, so interventions could be effective to get a person to comply with his prescription.

One indication of lack of compliance is whether a patient refills a prescription on time. This information is known to the pharmacy where the prescription was first filled, but may not be generally to the health care system in which the patient is involved. Even if known, there is not a well known system for utilizing this information to obtain patient compliance, except perhaps for the individual pharmacy to send the patient a notice when he does not return on time to fill the prescription.

It would be a great benefit in assuring compliance with medication prescriptions if a particular patient's behavior in this regard could be predicted at some time well before too much time has passed since the due date for the refill of the prescription. It would be of even more benefit if a prediction of compliance were effective in cases where only a single prescription is required, and there is no intent to refill the prescription. Then some intervention could be taken at the time the medication is prescribed in order to improve the likelihood that the patient will take the medication as prescribed. It would also be beneficial to know which of several interventions are most effective in terms of encouraging compliance.

SUMMARY OF THE INVENTION

The present invention is directed to improving the ability of organizations to improve the compliance of patients with prescriptions by predicting, based on information available upon the filling of the prescription, which type of intervention will be most effective at getting patients to follow their prescriptions. As a result, the organization can intervene with the proper type of intervention very early. Further, one aspect of the invention is directed to predicting which patients are most likely to fail to comply with their prescription, so that intervention can be directed at these patients that are at high risk of non-compliance at the time the prescription is given. The intervention may be in the form of educational information, reminders, etc. Further, by being able to predict those most likely not to comply, the organization can focus its compliance intervention activities on those patients. This allows for efficient use of the organization's resources, since interventions do not have to be sent to those who are very likely to comply anyway. Further, various intervention techniques can be employed and their effectiveness tracked with the present invention, in a "champion-challenger" scenario, so that compliance efforts can be improved over time.

According to the present invention, the predictions of the interventions that will be most effective are made by creating electronic records for each patient and appending additional demographic information to each record. This information is obtained from commercial databases. Typically, the information includes the demographic information and can also include (1) pharmacy information, e.g., information typically received by a pharmacy when a prescription is placed; (2) clinical information about the patient, e.g., information from examinations conducted by health care providers (such as blood pressure, body temperature, pulse rate, respiration rate, height, weight, EKG, etc.); (3) patient reports, e.g., questions asked of patients by the health care provider or derived from surveys of patients by any number of organizations; and (4) medical records of diagnoses and treatment (e.g., associated ICD 9 codes, CPT-4 codes, etc.) With this information a model of patient response to various intervention messages is formed using regression analysis in which compliance with a prescription is the dependent variable, and a group of particular intervention messages and the demographic information are the independent variables. The result is a reasonable number of demographic clusters which respond best to certain of the messages. Each cluster has a model defined by the regression analysis which is in the form of a probability equation having the independent variables multiplied by weighting factors which represent the relative significance of the variable in predicting the result.

The most effective intervention messages are so-called "champion" messages, and they are the ones used to intervene with patients meeting the criterion for the related demographic cluster. In addition, the patient prescription or pharmacy information, and the demographic information (collectively "patient data") can be regressed with the compliance information to obtain a prediction of which patients are likely to comply with their prescription and which ones are not. Thus, the champion messages for a cluster can be utilized with those patients in the cluster who are most likely not to comply, thereby making the intervention most efficient.

New "challenger" intervention messages can be created. "Challenger" messages are messages created to take the place of the champion messages if they prove more effective. These challenger messages can be sent to selected groups of patients and additional compliance information collected. This additional information and the prior patient data is then made the subject of another regression analysis to see if the challenger messages are more effective with one of the clusters than the current champion message for that cluster. If a challenger proves more effective by creating more compliance, it becomes the new champion. Further, the regression analysis can be re-run with the champion and challenger messages in combination with the demographic information to establish new clusters, if they result in a higher compliance ratio.

As additional data, including compliance information, is obtained over time, the weighting of the various components of the patient data can be dynamically modified to improve the accuracy of the models as a means for predicting the best message for a cluster and the patients who are most likely to fail to comply. If the model is based on prescription intake data at the pharmacy, or on data available even earlier when the health care provider writes the prescription, the patient's compliance with the prescription can be predicted as a probability early in the patient's treatment, allowing the maximum time for intervention.

In an illustrative embodiment of the invention, an organization, e.g., a pharmacy, a chain of pharmacies, or a third party organization acting on their behalf, collects from customers (i.e., patients) traditional data on a customer or patient being treated for some disease or condition, sometimes referred to as "pharmacy data" or "prescription data." This pharmacy data, which includes information identifying the patient and the medication prescribed for him, is converted into electronic form, e.g., with a data input terminal. This electronic data is stored in a database as patient records for later use.

In carrying out the invention, the procedure is to associate this patient data or information with (1) the effectiveness of a particular intervention, and/or (2) the probability of patient compliance with the medication prescription. This may be accomplished by a regression analysis carried out in a programmed digital computer which can access the patient records in the database. Each data element of patient data and various intervention messages are regressed in regard to the patient's compliance with the prescription, as best determined by the organization. The analysis suggests models of patient behavior in the form of the interventions that work best in effecting compliance, as well as models that predict compliance of a patient with a prescription or regardless of intervention. The models are in the form of probability equations which are the sum of each variable or element of the information multiplied by a weighting factor for that variable, as determined by the regression analysis.

It has been determined, however, that a more accurate model can be derived if additional variables are used to group patients into demographic clusters which are somewhat more homogeneous than the population at large. This is done through the use of additional demographic variables. Such additional variables can be derived from the basic patient information. For example, the patient's address, particularly the zip code, can be used to access databases of demographic information related thereto, e.g., average income, ethnic background, etc. of people living in that zip code. The purpose is to predict, based on past results, which intervention works best with which demographic cluster. Thus, when a new patient is to be subjected to an intervention, it is first determined which demographic cluster the patient belongs to, then the intervention most effective with patients in that cluster is sent to that patient.

Further, the most predictive clusters can be determined in a shorter period of time if logical choices are made of variables and combinations of variables which define the clusters. Some variables will have no predictive ability and will be discarded. The higher the predictive value, the larger the weighting factor. Further, assumptions can be made about which variables are the most important. The regression analysis can thus be made with regard to these variables first. If these variables are in fact important with regard to predicting compliance, the pharmacy may have some idea of the reasons for compliance or lack thereof, and can craft an intervention based on this information.

The models for the most effective intervention for a cluster and/or patient compliance, are stored as equations in the digital computer memory. Then as each patient's prescription data is input to the terminal, the computer uses the model equations to associate the patient with a cluster and/or create a score for the patient. The computer may be the same one that created the model or another one. For example,. the model may be created and then stored on personal computers located at the office of the health care provider or the pharmacy, which are also used to input patient information or prescription information. As an alternative the model could be on a remote computer in electronic communication with a personal computer at the pharmacy or office of the health care provider. While the present invention is not limited to any specific method of accessing the model, it may be done through the internet, an intranet or direct-link communication channels.

Depending on the cluster to which the patient is assigned by the computer, the patient will receive an intervention message that has been shown by the regression analysis to be most effective with members of that cluster. The message may be automatically generated and sent by the computer. If a patient compliance model has been created, and the application of the patient's information to this compliance model results in a patient's score that indicates a high probability that the patient will not comply with the prescription, the pharmacy, MCO, drug manufacturer or a third party representative of such organizations which service the patient, can intervene first with that patient to get him to follow the prescription. If resources are low, it may be that only high risk patients in a cluster receive the intervention.

The intervention may be by letter, fax, e-mail, Internet or a store and forward system (e.g., by pager). It may also be a phone call. While the intervention is typically a message of some sort, it may take some other form, e.g., an incentive awarded upon compliance. Regardless of the type of intervention, it may be automatically created and sent by apparatus used by the pharmacy, MCO, drug manufacturer or an organization administering the system for one or all of them. Further, the call or letter may be made to, or sent to, the patient, a spouse of the patient, the doctor of the patient and/or the employer of the patient, depending on which target of the intervention that experience has shown to produce the best results. The intervention information may be educational, e.g., warning of the consequences of not strictly following the prescription, and/or a notice that the medication needs to be taken or the prescription refilled.

The pharmacy or MCO can continuously collect data on patients and periodically use it to redo the regression analysis in an attempt to improve the models by basing them on more data. Also, the type of intervention can be a varied. Thus, the current best intervention, i.e., the champion, can be tested with a challenger message, to see if it can displace the champion.

Therefore, the present invention is directed to intervention processes focused on the objective of increasing the patient's compliance with a prescription. The intervention processes form a seamlessly integrated system of patient tracking, education and continuous quality improvements driven by sophisticated data and behavior analyses.

BRIEF DESCRIPTION OF THE DRAWINGS

The foregoing and other features of the present invention will be more readily apparent from the following detailed description and drawings of illustrative embodiments of the invention in which:

FIG. 5 is a chart showing the relative predictive power of various data elements;

FIG. 6 is a chart of various interventions and their relative effectiveness;

FIG. 7 is a chart showing compliance rates for a population; and

FIG. 8 is a chart showing a comparison of compliance rates for two different demographic clusters of a population.

DESCRIPTION OF ILLUSTRATIVE EMBODIMENTS

Figure 1:
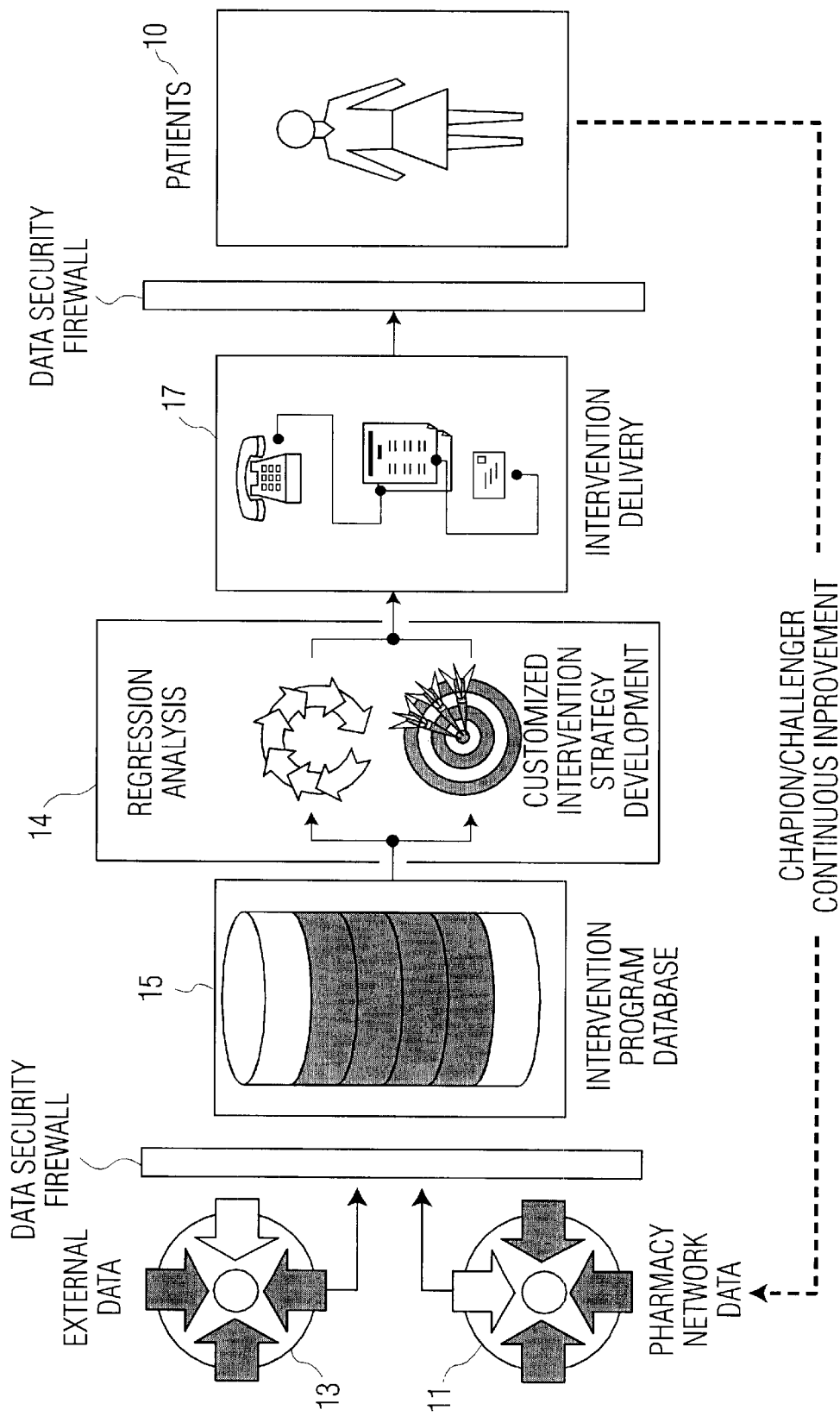
FIG. 1 is a schematic representation of the process flow for a prescription compliance system according to the present invention.

FIG. 1 illustrates in general a system for improving a patient's compliance with prescriptions. An organization, such as a pharmacy or chain of interconnected pharmacies, a drug manufacturer, a MCO or some other type of organization gathers typical data from patients 10. This includes information about the patient, e.g., name, address and perhaps age. In this example, the prescription is for medication so the data also includes "pharmacy data," such as the number of pills, the type of pills, the number of days supply, number of refills, etc. Further, the information may include the pharmacy location, and the name and location of the doctor who wrote the prescription. Based on this information, additional information can be obtained from the records of the pharmacy or health care provider. This includes, e.g., other disease states of the same patient, whether this or some other medication prescription was filled previously, whether it was refilled on time, whether the previous prescription or this one requires refills, the days since the last refill, the average days between refills, pharmacy claim data on the patient, such as national drug codes (e.g., NDC), the cost of the medication and the payment plan (all of which may be predictors of compliance). It is also possible to interrelate information on other family members who may be patients. The behavior of one family member in refilling prescriptions may be a good predictor of how other family members will behave in general or behave in response to a particular intervention. The sum of all this data makes up the pharmacy data.

In addition the present invention can also make use of"clinical data," such as height, weight, temperature, pulse rate, respiration rate, EKG, blood pressure, body fat, etc. Other useful information includes "medical claims" data in the form of the diagnosis made, which may be recorded in the form ICD 9 codes, and procedures used on the patient, which may be listed as CPT-4 codes. Even if no diagnosis is provided in the available data, it may be possible to imply a diagnosis from the medication prescribed and the doctor prescribing it. For example, information on the procedure used on the patient may be inferred and recorded in the form of ICD 9 codes.

"Patient report" data may also be included. This includes information the patient may be asked at the time the prescription is filled, information provided in patient surveys, and information in published research reports on patient behavior. One of these data segments or all of this information, i.e., the pharmacy, clinical, medical and patient report data, forms the pharmacy network data 11. This network data forms the basis for the "prescription data" from which "patient records" data is formed.

With the name and address of the patient 10, and possibly his social security number, it may be possible to collect general "demographic data" about the patient, e.g., whether he lives in an affluent neighborhood, and specific information about the patient (e.g., marital status, number of children, etc.) from commercially available databases 13. The external data 13 and the network data 11 can be combined into "prescription data" which may be stored in an intervention or compliance database 15 as "patient record," which are a collection of electronic data records on the population of patients using the pharmacy, enhanced with external data on the patients.

The intervention database 15 can be accessed by a processor 14, which may be a single digital computer or a group of computers, perhaps utilizing distributed processing over a LAN. This processor 14 uses the data in database 15 to determine whether the patient population is sufficiently homogeneous that members of the population are likely to behave in generally the same way as regards their response to various interventions that encourage compliance with prescriptions. If the population is not homogenous, the records for members of the population can be segregated into sub-populations or clusters which are more nearly homogeneous based on the demographic information. These clusters can be determined by reviewing the data, particularly the prior response of various patients with certain demographic factors to particular intervention messages. Clusters can also be determined based on prior experience, patient surveys and a review of relevant research papers. As an example, a male cluster and a female cluster may be suggested by the analysis due to the differences in the refill habits of men and women, It is well known that the behavior of large groups of people can be predicted based on data collected from the population over a period of time. One technique for making such predictions is based on modeling the behavior using regression analysis. While using these techniques will not invariably predict how an individual member of the population will behave, it can provide information on the probability that an individual will behave in a particular fashion. Such information can give the management of an organization involved in disease management some idea as to the characteristics of people most likely to behave in the predicted fashion, so that attention can be focused on that high probability group for some intervention to change the behavior.

According to the present invention, the processor uses regression analysis to define population clusters and to model the behavior of population clusters as regards their response to a variety of intervention messages. It may also model of the behavior of patients in a cluster as regards compliance in general, without regard to a particular intervention. These models are probability equations, each of which is the sum of the elements, or cross-products of the elements, of data that which have been shown to be predictive of response to a particular message or compliance behavior in general, each multiplied by its relative power to predict or "weight". To assist in the creation of the model, the organization using the present invention, in the present example a pharmacy, may conduct periodic surveys of patient's attitudes about particular messages or prescription compliance in general to determine the factors which play a major role in that behavior. This provides further insight into the behavior of patients and suggests the elements of data against which the regression should first be applied. The effect will be to arrive at a model faster than if variables are tried in a random fashion. Also, the survey results will suggest the reasons for non-compliance or failure to respond to a particular message, which will provide clues to the best interventions to overcome non-compliance.

Once the processor has established the clusters, the demographic factors that define membership in a cluster, and the intervention to which members of the cluster respond to best, future patients are automatically classified by cluster when they place a prescription. As a result, they receive the intervention associated with that cluster. However, this approach requires that all members of a cluster receive an intervention. This may be costly, so it is also within the scope of the present invention to use the processor to perform a regression analysis on patient information to determine those parameters that are predictive of the probability that the patient will comply with the prescription in general. Thus, if resources are limited, only those in a cluster with a high probability of non-compliance will be sent an intervention.

Application of the model for compliance by a patient in general to the data in a record for a single patient record, will result in a score for that patient which is a predictor of the patient's behavior as regards compliance. Compliance in general means that the patient will follow the prescription. However, in the pharmacy setting, the most that will be known is whether the patient filled or refilled the prescription reasonably on time. From this it is assumed that the prescription is or is not being followed. Nevertheless, it should be understood that this is no guarantee of strict compliance. A person appearing to comply may have lost the prescription, merely not taken the medication or taken it improperly, and still have refilled the prescription on time. Likewise, a person who appears not to have complied because he has not refilled the prescription at the pharmacy, may have refilled it at another pharmacy. Despite these shortcomings, the present invention can predict and influence compliance behavior over a large population. Also the specific compliance measured, i.e., refilling the prescription on time, bears a close relationship with actual compliance.

If the prescription is something other than medicine, the pharmacy data on prescriptions refilled will not indicate compliance. However, other behavior may be monitored to establish compliance. For example, if exercise is prescribed, records of attendance at a health club may indicate compliance. For those clubs which use electronic doors opened by magnetic cards or the entry of access codes, this compliance may be electronically indicated and may be automatically collected and used by the system. If the prescription requires that a patient stop smoking, compliance may be monitored by reports submitted by the patient. Further, if the patient makes purchases from stores using credit cards or similar devices, and permission is given, information on the patient's purchase of tobacco products could be monitored automatically to determine compliance, if the patient has a respiratory condition and monitors his lung function. This information can be provided to the organization as a self report, perhaps over the Internet, and used as an indication of compliance with a variety of prescriptions for that condition. Thus, prescription compliance as used herein is meant to be broader than merely following medication prescriptions.

The processor 14 is programmed to initiate intervention delivery 17, at least for those patients 10 with scores indicating a likelihood they will not comply with the prescription. This may be in the form of letters, educational materials or phone calls which have been shown to be particularly effective with members of the cluster to which the patient belongs.

If a patient who has received an intervention returns to the pharmacy for a refill, e.g., to the same or another store in a chain of pharmacies, additional information on the patient is obtained, e.g., the behavior of the patient in refilling the prescription. This information is added to the patient's record in the database and is used to improve the predictive model, and to assess the effectiveness of the interventions used across an entire population or within a particular cluster.

Figure 2:
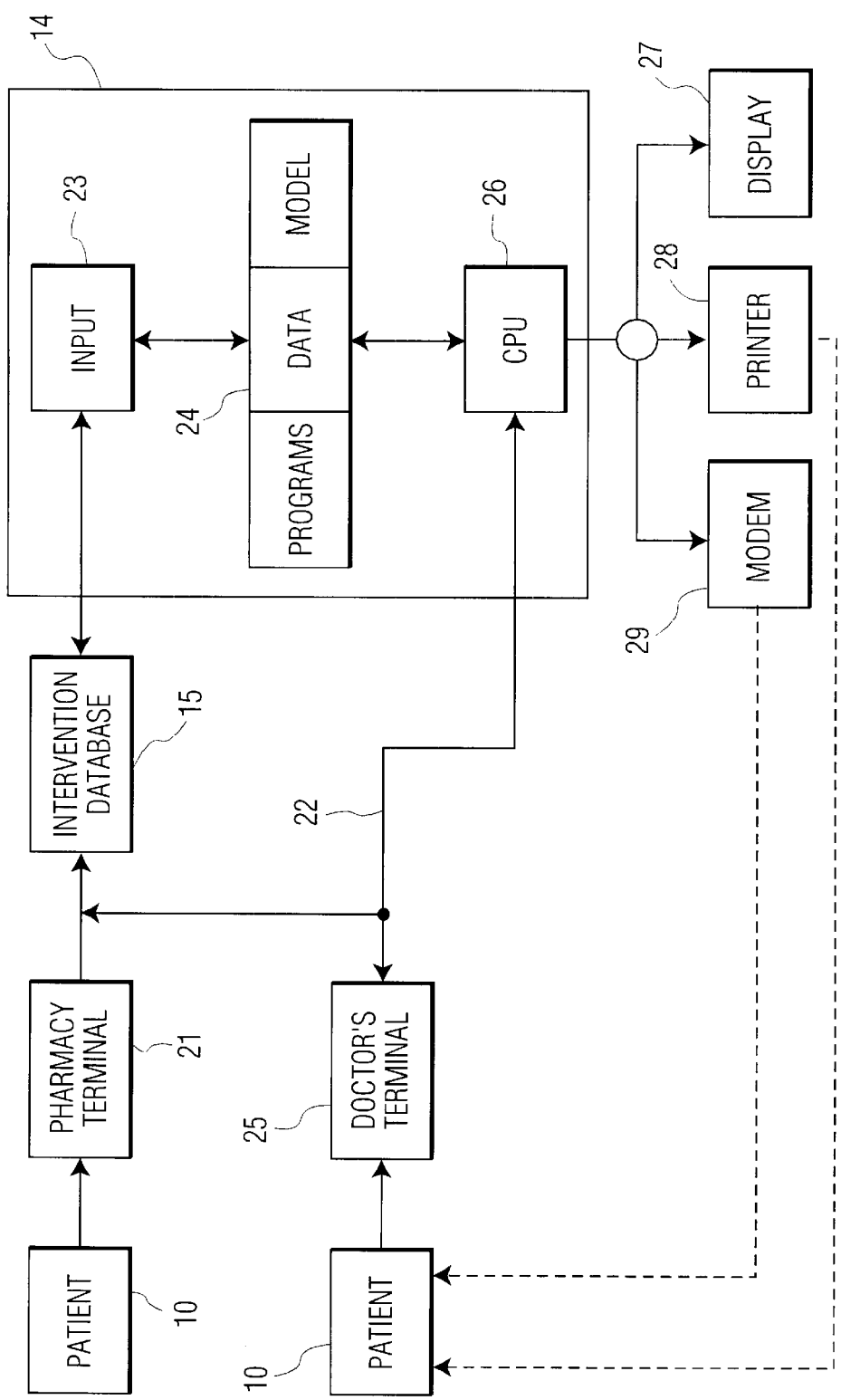
FIG. 2 is a block diagram of apparatus useful in carrying out the present invention.
Figure 3:
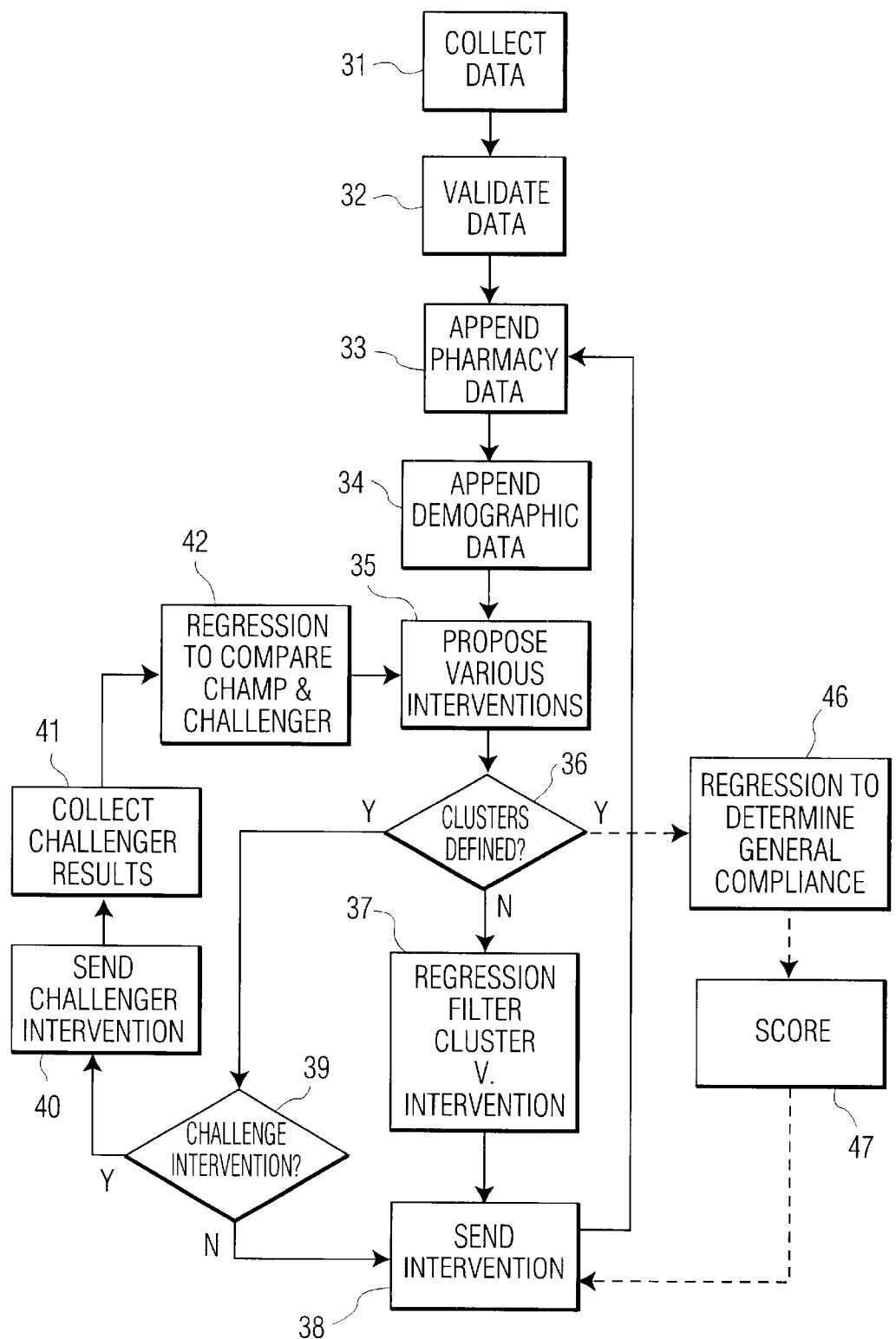
FIG. 3 is a flow chart of the operation of the processor of FIG. 2 when programmed for implementing a prescription compliance system according to the present invention.

FIG. 2 shows apparatus that can be used in practicing the present invention and FIG. 3 is a flow chart for the operation of the processor 14 of FIG. 2. The information collected from the patients 10 is converted into electronic form, e.g., by entering it into computer terminals 21 (step 31 of FIG. 3). Thus, an electronic record is created for each patient, which record contains a number of items of information. The data is then validated in step 32. This validation may be performed in the terminals 21, which may be personal computers, or in main processor 14, after the data records have been compiled in the intervention database 15.

Data validation is achieved through the use of data from commercial vendors, such as the Zip code+6 append database and the Post Office address correction database (National Change of Address processing and Group 1 software) based on the patient's address. Also, the government Drug Enforcement Administration ("DEA") file can be used to assign and validate physician numbers, and the American Medical Association ("AMA") database can be used to assign and validate physician's preferred mailing addresses. The National Council for Prescription Drug Providers file can be used to verify the names and addresses of pharmacies.

In step 33 of FIG. 3, the pharmacy data 11 is appended to the patient record. This is typically accomplished by having the pharmacy data loaded into database 15 directly or through one of the terminals, and then having the processor associate it with particular patient records. The pharmacy data includes the patient's name and address, the doctor's name and address, date of the prescription, pharmacy claim data on the patient, such as national drug codes (e.g., NDC), payment plan, etc. In addition, there is information on whether the prescription envisions refills. Further, the pharmacy will track whether prescription refills have previously been purchased on time. Other information can be inferred from the original data or collected from other sources, e.g., diagnosis, the procedure used on the patient (e.g., in the form of ICD 9 codes), the cost of the service, and hospital data on the patient (e.g., CPT codes).

Demographic data about the patient is selected from commercially available databases and is also appended to the patient records in step 34. This can be by way of direct connections between the database 15 and the remote commercial database or from the CPU 26 to the remote database via modem 29, or by other well known means. Examples of these commercial databases are the Polk Household Level Demographic database, Census Area databases and Donnelly databases. These can provide general information such as average income of people in the zip code, home ownership, etc. Also, it may be possible to find out specific information about the patient, e.g., marital status, number of children, education, employment, etc. The combination of all of this data is the "patient data" used in the present invention.

Various interventions are proposed for the patient population in step 35. These may take the form of various letters worded in various different ways, e-mail or phone calls. They may encourage the taking of the medication as a means to achieve better health, warn of the dangers of not taking it, or merely provide general educational information. The intervention may occur at various times, e.g., before the refill is due or after.

If the system has not yet determined which interventions are effective with which demographic clusters of patients as determined in step 36, the system passes through step 37 because it does not have sufficient information to make a model of patient behavior. As a result, the proposed interventions are merely sent to a wide variety of patients in step 38. The results of these interventions on patient behavior as regards compliance with the refill schedule for the prescriptions are collected and become part of the pharmacy data. On a subsequent pass through steps 31–35, there is now sufficient data available for a regression analysis to be performed in step 37 to determine if there are logical clusters of population, based on the demographic information, which respond in a reasonably predictable manner to one proposed intervention as opposed to another. Parameters, such as the maximum number of clusters, can be set to lead to the selection of clusters in a reasonable period of time. In additional, analysis of the data or research may suggest clusters. For example, do males and females show a similar compliance rate when other factors are the same? Are patients with low cost medications more likely to refill them than patients with high cost medications? Further, the program looks for relationships among combinations of variables. For example, is there a relationship between how affluent the patient's neighborhood is (derived from the patient's zip code), the cost of the medication and compliance. Based on this analysis, processor 14 may segregate the population into various clusters and associate particular interventions with each in step 37.

In carrying out the regression analysis, some portion of the data records, e.g., about 70% of the data records in the entire population or sub-population, are used to create the model. The other portion, e.g., about 30%, is reserved as a control for validation of the model. Input control 23 of processor 14 which transfers or downloads patient and pharmacy information data to processor 14 may be as simple as magnetic tapes with the selected information recorded thereon. These tapes are then loaded into memory 24 of processor 14. However, input control 23 may be data access software and hardware that allows data from intervention database 15 to be electronically transferred over a LAN, WAN or Internet connection to memory 24 where it can be operated upon by a central processing unit CPU 26 of processor 14. In addition to storing the patient information, the memory 24 also stores a program for performing the regression analysis and determining the clusters, which program is executed by CPU 26.

Figure 4:
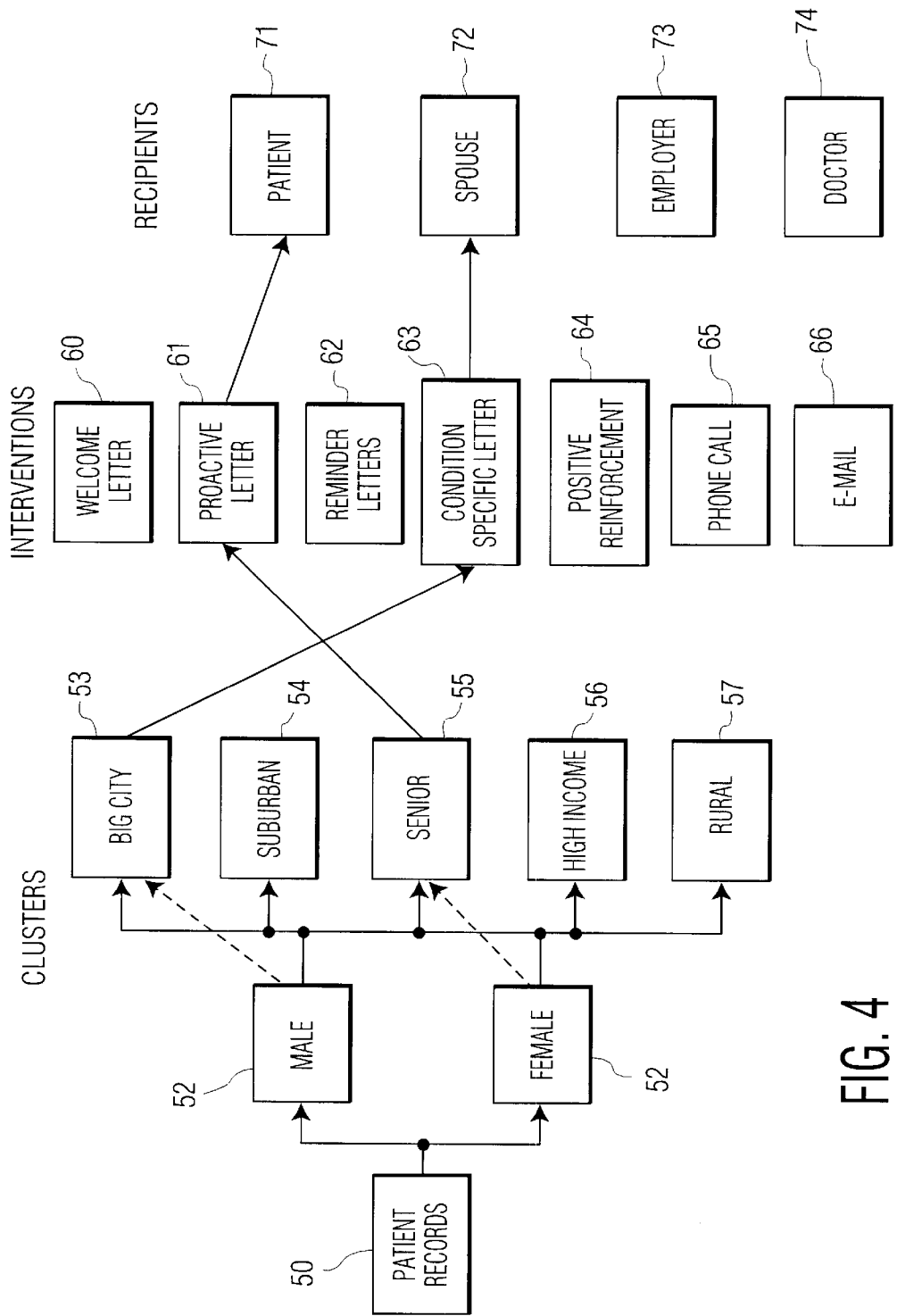
FIG. 4 is a chart showing the classification of the patient population into various typical demographic clusters and the association of these clusters with various interventions by the program of FIG. 3.

FIG. 4 shows various clusters which have been demonstrated to result in relatively predictable responses to particular interventions. For example, breaking the population of patient records 50 into male cluster 51 and female cluster 52 is effective because research shows that they respond to different messages. Examples of more refined clusters shown in FIG. 4 are:

Cluster 53—Big City (patients who live in urban areas, are less likely to be married or have children, are a mix of male/female heads of household, and are ethnically diverse);

Cluster 54—Suburban (married, male head of household, highest presence of children, highest percentage of truck owners, live in suburban/rural areas;

Cluster 55—Senior (likely to be retired, established residence, married home owners, high mail order activity;

Cluster 56—High Income (highest income, single family residence, highly educated, live in affluent areas, likely to have children present; and Cluster 57—Rural (reside in rural area, most mobile of clusters, likely to live in a multi-family dwelling, lowest income and education levels, least likely to be married).

Also shown in FIG. 4, are various proposed interventions such as a Welcome Letter 60 to patients who are new, i.e., filling a prescription for the first time. Other interventions are, e.g., a Proactive Letter 61 sent before the prescription is due for refill, Reminder Letter 62 sent after the refill date has passed and the prescription has not been refilled.

Instead of letters that simply remind the patient that the prescription is due for refill, the intervention message may contain information that is Condition Specific, such as Letter 63. For example, if the prescription indicates that the patient is suffering from asthma, the intervention message may warn about the specific consequences of not taking the medication. Research has shown that patients with a particular disease or condition tend to behave in certain predictable ways that are strongly related to the disease or condition. Thus, disease or condition specific information may get a fairly predictable response from various population clusters. Within this category are drug specific messages tailored for people taking a particular drug. Drug-specific intervention messages include: the importance of the prophylactic use of the drug, the effect of failure to take the drug on the patient's quality of life, the impact on the patient's productivity, control over his life, the seriousness of the condition, the minimizing of side effects, etc.

Rather than warning of dire consequences of failing to take the medication and refill the prescription, a form of message may be a Positive Reinforcement 64 in the form of congratulations on filling the prescription on time. Also, while written interventions are effective, other types are also effective, e.g., Phone Calls 65 or E-mail 66.

The process may also associate a recipient with the message. For example, the regression analysis may show that a particular message is effective with one cluster of patients if it is sent, not to the patient, but to the patient's doctor. Thus, FIG. 4 makes it clear that the recipient could be the patient 71, or the patient's spouse 72, employer 73 or doctor 74. As an example, the analysis may show by way of one arrow path in FIG. 4 that female members 52 of the Senior cluster 55 should have a Proactive Letter 61 addressed to them 71. However, a male 51, Big City cluster member 53 should have a Condition Specific Letter 63 sent to his spouse 72.

The formation of the clusters and the association of interventions with each cluster by means of regression analysis is referred to as Cluster Profile Analysis (CPA). Records within a cluster are similar to each other and are very different from those in other clusters, i.e., the CPA creates clusters that are homogeneous within a heterogeneous population.

In carrying out the regression analysis of step 37 (FIG. 3), the data in each record is organized into categories corresponding to potential variables. Then the variables and combinations thereof are tested for their ability to predict compliance with respect to the proposed intervention message the patient received. In particular, a subset of the patient information is selected to form a model of patient behavior based on the results of multi-variate statistical regression modeling, which selects the high relevance variables from the potential variables to predict whether a patient will comply with the prescription based on the intervention received. It also looks to classify respondents in to demographic clusters based on their response and the demographic information known about them.

In general terms, regression analysis involves "course classing." During this analysis, a count is made of the number of occurrences of an attribute (of patient information) for patients who have received a particular intervention and complied with their prescription, and those who have not. For each attribute having a sufficient number of counts for the compliant patients, the "Weight of Evidence" is computed by dividing the percentage of compliant patients by the percentage of non-compliant patients, and taking the natural logarithm of this quotient. The "information value" is the difference between the percentage of compliant patients and the percentage of non-compliant patients multiplied by the Weight of Evidence summed over every attribute. Attributes with high information values are considered candidates for inclusion in the predictive model. Groups of demographic variables which identify patients compliant with regard to a particular message are selected and used to define a cluster.

Preferably the predictive model is based on the results of logistic regression analysis. Logistic regression utilizes a regression model for binary (dichotomous) outcomes, and the data are assumed to follow binomial distributions with probabilities that depend on the independent variables. The probability equation is computed according to $$P = e^{logit}/(1 + e^{logit})$$

where P is the probability that a given patient will be compliant, e is a constant representing the base of natural logarithms, and logit is the sum of (I) a predetermined constant or weight and (ii) each of the high relevance variables multiplied by its respective coefficient. In other words, for n variables v used in the predictive model, the logit is computed as follows:

$$logic = (c_1 * v_1) + (c_2 * v_2) + (c_3 * v_3) + \ldots + (c_n * v_n) + \text{constant}$$

where $c_1$ is the coefficient corresponding to variable $v_1$, $c_2$ is the coefficient corresponding to variable $v_2$, etc. The coefficients are preferably logistic regression coefficients or weights which indicate the relative significance of the variable in predicting compliance in response to a particular intervention.

Returning to FIG. 3, during subsequent passes through steps 31–36, at step 36 the decision block will now indicate that the clusters have been defined. Thus, it is not necessary to preform step 37. Instead a determination is made in step 39 as to whether any new interventions were created in step 35 as challenges to the interventions that were previously associated with a cluster. If the answer is no, the system merely proceeds to step 38 in which the established or "champion" intervention is sent to patients depending on the cluster to which their demographic information assigns them.

If, however, in step 39 it is determined that there is a challenger, the system proceeds to step 40 in which challenge messages are sent to some members of the cluster or clusters, and champion messages are sent others (step 40). The results of both interventions are collected as regards compliance in step 41. Then in step 42 the regression analysis is run again to see if the challenger is more effective than the champion. If it is, the challenger is substituted for the champion and the system returns to routine operation, i.e., steps 31–36, 39 and then 38. With this routine operation, basically interventions are practiced with all patients. The only difference between them is that they may receive different interventions depending on the cluster to which they belong. This can be time consuming and expensive. A more efficient system would involve sending the champion intervention message for a cluster only to those patients in the cluster who are most likely to fail to comply with the prescription. In order to accomplish this, a regression analysis is made on the available patient information to determine which factors predict the likelihood the patient will be compliant.

Thus, in an alternative embodiment of the invention, if the clusters have been established, the model of patient behavior is formed in step 46 through the regression analysis. As shown in FIG. 3, the analysis is based on the cluster, so there is a separate behavior model for each cluster. However, it could also be based on the entire population. In particular, the items of data in a patient's record are used as variables to see their ability to predict compliance in general, which in this context means refilling a prescription on time. However, in other contexts, where compliance with a prescription can be checked in more detail, compliance may have a more detailed meaning, e.g., the medication was taken three times a day after meals or the patient went to the gym four times a week. In any event, each of the items of information, and perhaps combinations thereof, are tested for their ability to predict prescription compliance.

The memory 24 also stores a predictive model in the form of a probability equation based on the results of the regression analysis. The probability equation is, at least in part, the sum of each of the high relevance variables multiplied by their corresponding weighting coefficients. When patient data is used as the input to the equation, the result is probability values or scores for each patient which are indicative of the likelihood that the patient will comply with his prescription.

While it is possible to start with any one of the variables and work through the rest to arrive at predictive variables, this might lead to results which are not logical. For example, a correlation may be revealed between the first letter of the patient's name and compliance which is purely a quirk of the data used. Instead of taking this brute force approach, it is more efficient to first select the variables believed to be predictive based on some hypothesis for patient compliance. If this turns out to be a very predictive variable, than the hypothesis which suggested it provides some indication of the appropriate intervention to take in order to increase the likelihood the patient will comply. For example, if lack of compliance is believed to be due to the distance from a patient's home to the pharmacy, then this variable can be checked based on the addresses of the patient and the pharmacy. The intervention might be a notification to the patient of a new pharmacy or another pharmacy in his neighborhood.

The results of the regression analysis are evaluated and the least predictive of the potentially predictive variables from the patient data are eliminated. The multi-variate statistical regression modeling analysis is continued and the next least predictive of the potentially predictive variables is eliminated. This is repeated until each of the remaining variables has a significant value greater than a predetermined threshold.

Once the regression analysis has been completed, a preliminary predictive model of the behavior or the patients as regards prescription compliance is created. The model depends on the remaining variables and is a probability equation based at least in part on the sum of each of the remaining variables multiplied by its corresponding weighting coefficient. Using the equation with the data for each patient, scores for the patient are generated (FIG. 3, step 47) which indicate the patient's probability of compliance. Thus, the model, which is the result of the logistic regression analysis, optimizes the score differential between those patients complying with their prescriptions and those who do not.

One way to determine if the predictive model is accurate is a statistical measure called "divergence." Divergence is a measure of the strength of the predictive attributes or variables, and is the square of the difference between the mean scores of the compliant and non-compliant patients, divided by their average variance. It basically tells how well the model is separating the compliant patients from the non-compliant patients, so the greater the divergence, the better the predictive value of the model. In practice, divergence is typically between 0.3 and 2.0 and the weights associated with each attribute in the model are chosen to optimize the score divergence. It may also be useful to place weight pattern restrictions on the variables to reduce the effects of inter-correlations among variables that produce incorrect model coefficients.

The variables that were not selected for the initial model because of low information values can be evaluated for their possible contribution to the model. This is done by determining if they improve divergence. This individual improvement in divergence is called the "marginal contribution to the characteristic." Any strong contributors among the low information characteristics which were not used before are added to the model, while poor contributors are removed. Some of these poor contributors may in fact be predictive in themselves, but are highly correlated to one or more of the other characteristics in the model. This process is repeated until the marginal contribution for each non-used characteristic is negligible.

While it is preferable to use multi-variate logistic regression analysis modeling with the present invention, other types of regression analysis also may be used, such as linear regression analysis. Various commercial statistical software packages for performing regression analysis are readily available, such as SAS offered by SAS Institute, Inc. of Cary, N.C.; STATA offered by Stata Corporation of College Station, Tex.; or SPSS offered by SPSS Inc. of Chicago, Ill. For further information on regression techniques useful in the practice of the present invention, see Michael J. A. Verry and Gordon Linoff, *Data Mining Techniques,* Wyley Computer Publishing (1997).

FIG. 5 illustrates a probability equation used in conjunction with the patient data records to arrive at a probability score for each patient in a cluster segregated on the basis that they are filling a prescription for the first time. The score for each patient is indicative of the likelihood that the patient will comply with his or her prescription. In FIG. 5, "Number of Refills Allowed" under the current prescription is a predictive parameter and has a weight of 0.114. The "Number of Days Supply" in the current prescription is also a predictive variable with a weight of 0.013. The sum of each of the listed data variables from the patient's record multiplied by the predictive power or weight, will give the patient score. In other words, the equation predicts the likelihood or probability that the member will comply with the prescription in a given period of time relative to other patients. This is calculated by having each record scored by CPU 26, i.e., each record is given a score value as determined by the model (step 47 of FIG. 3). This score is stored in memory 24

(FIG. 2) along with the other information in a patient record. The score and other relevant information may be formed into reports and displayed on display 27 to the operator of the system (FIG. 2). This information may also be printed on a printer 28.

Once it is known, based on a patients' scores, which patients are not likely to refill their prescriptions, a decision can be made whether to send the champion intervention for the cluster to all patients in the cluster or only those with a score beyond a predetermined value indicating an unacceptable probability of non-compliance. Then the interventions are sent to improve the probability of compliance by members of the cluster. (Step 38 of FIG. 3). The intervention may be in the form of a reminder letter sent to the patient telling them of the need to refill the prescription and the benefits of doing so. This letter can be automatically generated by system 25 and printed by printer 28. In addition, the intervention may be in the form of an e-mail that is generated by system 25 and sent to the member's e-mail address over the Internet by modem 29. As an alternative, a pre-recorded or digitally composed voice message may be created by system 25, the phone number of the patient dialed by the modem 29, and the message played when the phone is answered. In addition to, or as an alternative, the patient's spouse, employer or doctor may be contacted for the intervention. This is illustrated in FIG. 4.

The type of intervention message sent is based on the cluster to which the patient is assigned, which is the message that has been determined to be most effective by an analysis of the patient's record. This selection of specialized messages may be performed automatically by system 25. Also, interventions may be cumulative. For example, if a high-risk patients has ignored one or more mailings, they can be identified to the pharmacy so they can be contacted by telephone.

It is important to test the effectiveness of the invention in predicting the ability of certain interventions to increase compliance in certain patient population clusters, and predicting patient compliance in general so that modifications to the models can be made as needed. To accomplish this, intervention is withheld from a randomly selected group of members. The compliance rate of these patients is then compared to the control group, i.e., the portion of the overall population that was set aside at the beginning of the process. This should show the power of the models to predict compliance versus the average for the population, and will justify application of the invention. Through this technique as well as patient surveys, the effectiveness of individual interventions can be determined, e.g. as shown in FIG. 6. In particular FIG. 6 shows the relative effectiveness of different types of messages in promoting compliance compared to a control group in which no interventions was made.

In many cases a rough prediction of patient compliance can be made on the basis of initial prescription data (see FIG. 5). As a result, intervention may begin with patients most likely to fail in compliance as soon as the prescription is placed with the pharmacy. This gives the interventions the maximum time to be effective. In one embodiment of the apparatus of FIG. 2, assuming the model or models have been created previously, the information from the patient 10 is input at terminal 21 at the pharmacy. This information is immediately transferred by modem to CPU 26 over line 22. The CPU 26 calculates the patient's score and may assign the patient to a demographic cluster, assuming the necessary demographic factor are known or are supplied by the patient. The score and cluster information is then returned to terminal 21. As an alternative, the probability equations for the score and cluster can be stored in terminal 21, and the score and cluster assignment can be calculated in that computer. In either event, the pharmacist can determine if the patient is likely to comply even before the patient leaves the store. Consequently, th e pharmacist can provide verbal encouragement to the patient to take and refill the prescription, and can give the patient previously prepared educational materials appropriate to someone in his cluster. If a printer is part of terminal 21, the system can cause the printer to print the latest champion message for patients in the cluster and the pharmacist can give it to the patient along with the prescription.

Similarly, a terminal 25 may be located at the doctor's office. If prescription information is entered on that terminal, perhaps in connection with the generation of a bill, a healthcare provider at the doctor's office can also make an intervention based on the patient's score. As in th e case of the pharmacy, the score is obtained by the use of a probability equation in the terminal 25, or by transferring the patient data by modem or the Internet over line 22 to the CPU 26, which scores the patient and returns the information to terminal 25 so an intervention can be made even before the patient leaves the doctor's office. The intervention used will depend on the demographic cluster to which the patient belongs.

Information on the compliance is made a part of the patient's record. Periodically, as new data is gathered, the regression analysis of general patient compliance is run again and the model is refined. Refining of the model may be due to the inclusion of more information which is similar to the prior information, or it may also include information on the intervention that was employed so as to determine its effect on patient compliance.

The scoring of the patients, as shown in step 47 of FIG. 3, may include scaling of the scores so that odds of e.g. 0.55 (number of compliant/number of non-compliant) corresponds to a score of zero. A score greater than zero means that a patient will be more likely to comply than average, and a score less than zero (i.e. a negative score) means that the patient will be less likely than average to comply. The scores can be scaled so that odds double every 50 points, which means that a member scoring 50 will be twice as likely to comply as someone scoring 100. Since scores are scaled the same way, a score reflects the same odds across clusters.

The scaling can be arranged by assigning weights to ranges of values for each item of data so they cover the full range of possible values for that attribute. Examples for a cluster called "First Fill" for parameters called "Number of Refills" and "Number of Days Supply" (FIG. 5) are as follows:

| No. of Refills | Patient Score | No. of Days Supply | Patient Score |
| --- | --- | --- | --- |
| 1 | −23 | 1–19 | −23 |
| 2 | +21 | 20–29 | −19 |
| 3 | +27 | 30+ | −4 |
| 4–6 | +41 | No Info | −7 |
| 7–98 | +45 | | |
| 99 | +17 | | |
| No Info | +18 | | |

Arranged below is a scorecard for a hypothetical patient who is first filling a prescription and who is scored according to the scorecard of FIG. 5, which has been scaled as shown above. In the scorecard the value of each characteristic is displayed under the name, and to the right there is the number which represents the weight associated with that characteristic. The score is obtained by adding up weights as follows:

| Characteristic | Patient Data | Weight |
|---|---|---|
| Number of Refills Allowed Current Rx (1 falls into class −23) | 1 | −23 |
| Number of Days Supply Current Rx (30 days is in class −4) | 30 | −4 |
| Age of Patient (30–34 years is in class 5) | 30 | +5 |
| Seasonal Letter Sent in Past (y/n) (No is in class −23) | No | −23 |
| Month of Current Fill (Oct. & Nov. in class −14) | October | −14 |
| Store State (Iowa, Ill, Ind., Wisc. are in class +13) | Iowa | +13 |
| Quantity Dispensed (30 falls into class −8) | 30 | −8 |
| Day of the Week of Current Fill (Wed.–Fri. are in class −3) | Thursday | −3 |
| Score (Sum of Characteristic Weights) | | −57 |

Once a scaled score is calculated, it may be converted to odds, which represent the number of compliant patients for each non-compliant patient in the overall population or cluster. The conversion of the score to odds is as follows:

$$ODDS = 0.55 \times 2^{score/50}$$

Thus for a score of −57, the odds would be $$ODDS = 0.55 \times 2^{-57/50} = 0.25.$$

This means that for every 5 patients that have a score of −57, there will be 4 patients who are non-compliant for each patient that is compliant.

The system can provide reports to the pharmacy on the scores of each patient, together with other information gathered from the patient data. This information can be in the form of written reports generated on printer 28 or displays on display 27, or one or more of the terminals 21. The reports can, for example, compare the behavior of patients who participated in the intervention program with those of a control group of non-participating patients. Comparisons are made between the two groups over a defined period of time with regard to prescription units sold, prescription refill pick-up percentage, days of medication purchased, and persistence percentage over a defined period of time. Thus, the reports can indicate the effectiveness of the intervention program.

The is no clear indication when the accuracy of the model has been maximized through new data recycled through the system, including new data on compliance. However, the table of FIG. 7 shows the predictive strength of a model that has proven useful, i.e., the model of FIG. 5. In particular, FIG. 7 shows that the members with the top 10% of scores as determined by the model complied 10% of the time, while those with the lowest 10% complied 71% of the time. The average compliance rate was 32%. This is considered to be an acceptable level of performance according to the present invention.

The effect of forming the data into clusters is shown in FIG. 8. One cluster was patients filling a prescription for the first time. The other cluster was patients filling a prescription two or more times. It can be seen that the variation in rates is greater for the Second Fill group, because the model is better able to predict behavior in that group, so there is a greater diversity. For example, for those First Fill patients with scores in the lowest 10%, the model predicts 39% of those who comply. However, for the Second Fill patients, the model predicts 79% of those who will comply.

In addition to letters and phone calls, the interventions can include messages sent over the Internet in the form of, e.g., an interactive allergy web site, an allergy web page, e-mail (with text, sound and/or video) chat rooms, etc. It may also include information at the Point-of-Care, e.g. the doctor's office, Newsletters, Interactive Cable television, a Help Desk, etc. Patient surveys, provider feedback, reports and other measurement tools may help the organization track performance.

In a further alternative embodiment of the present invention a company, e.g. a pharmaceutical company, encloses coupons with its products which request the name and address of the person using the coupon to purchase one or more of its products. When the coupons are filled out and used to make a purchase, they are returned to the company by the retail outlet for redemption. The company then uses the coupons to create a database of customer information with plural records that include the name, address (including zip code) and drug purchased.

Based on the information in the customer records, additional demographic information is obtained, e.g. from commercial databases, on the individual and is included in the customer records.

A group of letters are then generated which encourage the further purchase of the product. These may be in the form of marketing letters intended to create brand awareness and loyalty, instead of, or in addition to, messages of a clinical nature which stress the benefits of taking the particular medication. This is of particular importance if the product is required over a long period of time, or even for life, to control a chronic condition. These letters would include additional coupons to be redeemed in the same fashion as the original coupons. In this way, the customer database would be updated with information on how successful the various letters were in prompting the further purchase of the product.

Using regression analysis on the enhanced customer database, a model could be used to cluster respondents according to demographic information and their response to particular letters. In the future, when a new customer returns an original coupon, the available demographic information on that customer is accessed, the customer is assigned to a cluster as a result thereof, and the customer is sent the follow up letter with new coupons that has proved most effective with customers in that cluster.

As additional information is obtained over time, the model can be refined. Further, new letters can be created and the results of their use are tracked. If the new letters prove more successful than the old letters, the challenger (new) letters are substituted for the old (champion) letters for use with that cluster.

While the present invention has been particularly shown and described with reference to preferred embodiments thereof, it will be understood by those skilled in the art that various changes in form and details may be made therein without departing from the spirit and scope of the invention which is defined solely by the appended claims.

We claim:

1. An apparatus for effecting a patient's compliance with a prescription, comprising:

a) at least one data processing terminal through which patient prescription data is collected on patients in electronic form, said terminal collecting the data in the form of records for each patient, each patient record including at least an identification of the patient and the prescription;

b) a database in the form of an organized memory in which the patient records are stored;

c) a predictive computing system including a processor, a processor memory and an electronic access device by which said processor accesses the patient records in said database, said processor memory storing a regression analysis program which operates in said processor on the various elements of data in the patient record;

d) said processor memory storing intervention data in electronic form which at least generally indicates patient prescription compliance in the form of the response of various patients to various predetermined intervention messages, said messages being intended to get patients to comply with their prescription;

e) said processor appending said intervention data to related patient data in said patient records; and f) said processor using said regression analysis program to create automatically an intervention model using the data in said patient records including said intervention data, said intervention model indicating a segregation of the patient records into clusters based on said patient information and an association of each cluster with a champion intervention which is the predetermined intervention which is most effective in causing patients in that cluster to behave so as to create a general indication of compliance; and g) an output device by which the intervention is at least in part delivered.

2. Apparatus according to claim 1 wherein said access device obtains demographic information on said patients from remote databases and said processor associates the demographic information with the related patient record and forms said patient clusters based on said demographic information.

3. Apparatus according to claim 1 wherein a) said database further includes compliance information for at least some of the patients in the form of data indicating the compliance of patients with prescriptions without an intervention; and b) said processor appending said compliance information to related patient records, creating a compliance model based on patient data for predicting which patients will comply with a prescription, said compliance model being created by regression analysis of the compliance information with regard to the other data in the patient records, and assigning a score to each patient record based on the model, said score being a prediction of the relative likelihood that a patient will comply with his prescription.

4. Apparatus according to claim 1 wherein said various interventions include champion interventions from a previous regression analysis and a challenger intervention, said processor substituting a challenger intervention for a champion intervention whenever said regression analysis indicates greater compliance of the cluster population in response to the challenger intervention.

5. Apparatus for effecting a patient's compliance with a prescription, comprising:

a) at least one data processing terminal through which patient prescription data is collected on patients in electronic form, said terminal collecting the data in the form of records for each patient, each patient record including at least an identification of the patient and the prescription;

b) a database in the form of an organized memory in which the patient records are stored, said database further storing compliance information for at least some of the patients in the form of data indicating the previous compliance of patients with prescriptions without an intervention; and c) a predictive computing system including a processor, a processor memory storing a regression analysis program which operates in said processor on the various elements of data in the patient record, and an electronic access device by which said processor accesses the patient records in said database, said processor appending said compliance information to related patient records and automatically creating a compliance model based on patient data for predicting which patients will comply with a prescription, said compliance model being created by regression analysis of the compliance information with regard to the other data in the patient records using the regression analysis program, said processor assigning a score to each patient record based on the model, said score being a prediction of the relative likelihood that a patient will comply with his prescription.

6. Apparatus according to claim 5 further including an output device by which the intervention is at least in part delivered.

7. The apparatus of claim 6 wherein the processor causes the output device to generate an intervention message and send it at a predetermined time.

8. The apparatus of claim 6 wherein the output device is one of a printer and modem, and wherein the printer creates and sends a printed intervention message, and the modem sends one of an audio or video message, including an e-mail.

9. The apparatus of claim 6 wherein the output device is one of a display, printer and modem.

* * * * *